(12) United States Patent
Toh et al.

(10) Patent No.: US 11,786,171 B2
(45) Date of Patent: Oct. 17, 2023

(54) METHOD AND SYSTEM FOR ARTICULATION EVALUATION BY FUSING ACOUSTIC FEATURES AND ARTICULATORY MOVEMENT FEATURES

(71) Applicant: XIAMEN KUAISHANGTONG TECH. CORP., LTD., Fujian (CN)

(72) Inventors: Takeshi Toh, Ishikawa (JP); Meng Yuan, Fujian (CN); Longbiao Wang, Fujian (CN)

(73) Assignee: XIAMEN KUAISHANGTONG TECH. CORP., LTD., Fujian (CN)

( * ) Notice: Subject to any disclaimer, the term of this patent is extended or adjusted under 35 U.S.C. 154(b) by 839 days.

(21) Appl. No.: 16/616,459

(22) PCT Filed: Sep. 17, 2018

(86) PCT No.: PCT/CN2018/105942
§ 371 (c)(1),
(2) Date: Nov. 23, 2019

(87) PCT Pub. No.: WO2019/034184
PCT Pub. Date: Feb. 21, 2019

(65) Prior Publication Data
US 2020/0178883 A1 Jun. 11, 2020

(30) Foreign Application Priority Data
Aug. 17, 2017 (CN) .......................... 201710708049.6

(51) Int. Cl.
*A61B 5/00* (2006.01)
*G10L 25/60* (2013.01)
(Continued)

(52) U.S. Cl.
CPC ............ *A61B 5/4803* (2013.01); *G10L 25/60* (2013.01); *G10L 25/03* (2013.01); *G10L 25/24* (2013.01)

(58) Field of Classification Search
CPC ... A61B 5/4803; A61B 5/1114; A61B 5/1121; A61B 5/682; A61B 5/7267;
(Continued)

(56) References Cited

U.S. PATENT DOCUMENTS 4,836,218 A * 6/1989 Gay .......................... G01H 1/00
600/595
8,290,277 B2 * 10/2012 Hwang ................ G06V 40/165
382/254

(Continued)

FOREIGN PATENT DOCUMENTS

| CN | 101292281 A | 10/2008 |
|---|---|---|
| CN | 102063903 A | 5/2011 |

(Continued)

*Primary Examiner* — Amine Benlagsir
(74) *Attorney, Agent, or Firm* — John Alumit

(57) ABSTRACT

The present invention provides an articulation evaluation method and system combining acoustic features and articulation motion features. According to the articulation evaluation method and system, audio data and articulation motion data are acquired, acoustic features are extracted from the audio data, articulation motion features are extracted from the articulation motion features, and feature fusion and policy fusion are performed on the acoustic features and the articulation motion features according to a time correspondence, which effectively utilizes the complementarity of the two types of features to ensure the objectivity and comprehensiveness of evaluation, so that a more accurate and reliable feature fusion evaluation result and decision fusion evaluation result are obtained, making the articulation evaluation more objective and accurate.

10 Claims, 3 Drawing Sheets

(51) Int. Cl.
*G10L 25/24* (2013.01)
*G10L 25/03* (2013.01)

(58) Field of Classification Search
CPC .... A61B 2562/0204; A61B 2562/0219; G10L 25/60; G10L 25/03; G10L 25/24
See application file for complete search history.

(56) References Cited

U.S. PATENT DOCUMENTS

| | | | | |
|---|---|---|---|---|
| 8,913,103 | B1* | 12/2014 | Sargin | G06V 40/16 348/14.12 |
| 2013/0226587 | A1* | 8/2013 | Cheung | G10L 15/25 704/273 |
| 2014/0342324 | A1* | 11/2014 | Ghovanloo | G09B 5/06 434/185 |
| 2014/0365221 | A1* | 12/2014 | Ben-Ezra | G10L 15/25 704/256.1 |
| 2015/0213604 | A1* | 7/2015 | Li | H04N 7/147 345/473 |
| 2016/0199203 | A1* | 7/2016 | Adachi | A61F 4/00 600/383 |
| 2017/0100069 | A1* | 4/2017 | Edwards | A61B 5/11 |
| 2019/0116395 | A1* | 4/2019 | Kerdranvat | H04N 21/8358 |

FOREIGN PATENT DOCUMENTS

| | | |
|---|---|---|
| CN | 102663928 A | 9/2012 |
| CN | 103218924 A | 7/2013 |
| CN | 106409030 A | 2/2017 |
| CN | 107578772 A | 1/2018 |
| JP | 2012088675 A | 5/2012 |
| WO | WO 2015030471 A1 | 3/2015 |

* cited by examiner

METHOD AND SYSTEM FOR ARTICULATION EVALUATION BY FUSING ACOUSTIC FEATURES AND ARTICULATORY MOVEMENT FEATURES

TECHNICAL FIELD

The present invention relates to the field of articulation evaluation technologies, and in particular to an articulation evaluation method combining acoustic features and articulation motion features and a system using the same.

BACKGROUND

The perception and generation of speeches is the result of multiple auditory organs and vocal organs working together in a short period of time. Some people suffer from congenital and traumatic brain or nerve injury, so that it is impossible to control specific muscles to emit a correct speech, which is characterized by abnormal articulation, sound production, resonance and rhythm. This is dysarthria.

The speech intelligibility is the degree to which a listener can accurately obtain information expressed by speech signals of a speaker, and articulation evaluation is often performed on the severity of dysarthria through the speech intelligibility. The more serious the disease is, the lower the intelligibility of the speech is. In recent years, the research on dysarthria has gradually increased, but most of the research uses acoustic parameters to analyze the intelligibility, ignoring that abnormal movements of vocal organs are the source of abnormal sounds. As a result, an evaluation method is not comprehensive enough, and an evaluation result is not reliable. Therefore, it is especially important to develop a set of reliable and objective and accurate evaluation criteria that do not depend on subjective evaluation.

SUMMARY

In order to solve the above problems, the present invention provides an articulation evaluation method and system combining acoustic features and articulation motion features. According to the articulation evaluation method and system, audio data and corresponding articulation motion data are acquired, acoustic features and corresponding articulation motion features are extracted respectively, and fusion processing is performed on the acoustic features and the articulation motion features, so that a more accurate and reliable fusion evaluation result is obtained, which makes the articulation evaluation more objective and accurate.

In order to achieve the above objective, the technical solution adopted by the present invention is:

An articulation evaluation method combining acoustic features and articulation motion features includes the following steps:

step (10): acquiring audio data and articulation motion data, extracting acoustic features from the audio data, and extracting articulation motion features from the articulation motion data, where the audio data and the articulation motion data correspond in time;

step (20): performing feature fusion processing on the acoustic features and the articulation motion features according to a time correspondence to obtain fusion features;

step (30): performing training according to the fusion features to obtain a fusion feature intelligibility discrimination model; and step (40): obtaining a feature fusion evaluation result by using the fusion feature intelligibility discrimination model.

Preferably, further, training is respectively performed according to the acoustic features and the articulation motion features to obtain an acoustic feature intelligibility discrimination model and an articulation motion feature intelligibility discrimination model, and policy fusion processing is performed on an evaluation result of the acoustic feature intelligibility discrimination model and an evaluation result of the articulation motion feature intelligibility discrimination model to obtain a policy fusion evaluation result.

Preferably, the acquiring audio data and articulation motion data in step (10) is to acquire the audio data and the articulation motion data by using an electromagnetic articulation motion tracing system, obtain the articulation motion data by placing space sensors at a vocal organ and calculating three-dimensional space coordinates and angles of the space sensors in a magnetic field, and acquire the audio data corresponding in time while acquiring the articulation motion data; where the vocal organ includes lips, and the articulation motion data includes lip motion data.

Preferably, further, a space sensor is placed on a nose bridge, and the extracting articulation motion features from the articulation motion features in step (10) is to use the space sensor on the nose bridge as a coordinate origin, and calculate relative distances between space sensors on lips and the coordinate origin; use three-dimensional coordinate distances x, y, and z of four space sensors on the lips as motion features, use each sampling point as a frame, and extract articulation motion features from each frame of data according to the following formula:

$$\text{lip} = [x_1 \ldots x_4, y_1 \ldots y_4, z_1 \ldots z_4]^T;$$

where subscripts of, x, y, and z represent upper lip motion data, lower lip motion data, left mouth corner motion data, and right mouth corner motion data, respectively.

Preferably, the performing feature fusion processing in step (20) is to set a window length of the audio features and the articulation motion data according to a sampling rate of the audio data and the articulation motion data, set a window move according to the window length, and perform feature fusion on the acoustic features and the articulation motion features through the window move.

Preferably, the policy fusion processing is to set different weight ratios according to an evaluation result of the acoustic feature intelligibility discrimination model and an evaluation result of the articulation motion feature intelligibility discrimination model respectively, and calculate a policy fusion evaluation result according to the weight ratio; a calculation method is as follows:

$$LL = \underset{k}{\mathrm{argmax}} \{w \times LL_{acoustic}^k + (1-w) \times LL_{articulatory}^k\};$$

where LL represents the policy fusion evaluation result; $LL_{acoustic}^k$ represents an evaluation result of the acoustic feature intelligibility discrimination model, $LL_{articulatory}^k$ represents an evaluation result of the articulation motion feature intelligibility discrimination model, k represents grade classification of the evaluation results, w represents a weight, and an argmax function represents looking for a parameter with a largest score.

Correspondingly, the present invention also provides an articulation evaluation system combining acoustic features and articulation motion features, including:

a feature extraction module, configured to acquire audio data and articulation motion data, extract acoustic features from the audio data, and extract articulation motion features from the articulation motion data, where the audio data and the articulation motion data correspond in time;

a feature fusion module, configured to perform feature fusion processing on the acoustic features and the articulation motion features according to a time correspondence to obtain fusion features;

a model training module, configured to perform training according to the fusion features to obtain a fusion feature intelligibility discrimination model; and an articulation evaluation module, configured to obtain a feature fusion evaluation result by using the fusion feature intelligibility discrimination model.

Preferably, the articulation evaluation system further includes a policy fusion module;

the model training module further respectively performs training according to the acoustic features and the articulation motion features to obtain an acoustic feature intelligibility discrimination model and an articulation motion feature intelligibility discrimination model; and The policy fusion module performs policy fusion processing on an evaluation result of the acoustic feature intelligibility discrimination model and an evaluation result of the articulation motion feature intelligibility discrimination model to obtain a policy fusion evaluation result.

Preferably, the articulation evaluation system further includes a data acquisition module, where the data acquisition module acquires the audio data and the articulation motion data by using an electromagnetic articulation motion tracing system, obtains the articulation motion data by placing space sensors at a vocal organ and calculating three-dimensional space coordinates and angles of the space sensors in a magnetic field, and acquires the audio data corresponding in time while acquiring the articulation motion data.

Preferably, the vocal organ includes one or more of the following: a tongue, lips, mouth corners, and incisors; where space sensors of the tongue are disposed at the tip of the tongue, the center of the tongue, and the back of the tongue; space sensors of the lips are disposed at the middle of the upper lip and the middle of the lower lip; space sensors of the mouth corners are disposed at the left mouth corner and the right mouth corner; and space sensors of the incisors are disposed on lower incisors and used to track movements of a jaw.

Further, the articulation evaluation method also includes setting a space sensor at a head position to detect head motion data, and correcting the articulation motion data according to the head motion data; where the head position includes one or more of the following: a forehead, a nose bridge, and ear backs; where the space sensors of the ear backs are disposed on mastoid bones at the ear backs.

Preferably, the model training module performs training by respectively inputting the acoustic features, the articulation motion features or the fusion features into a Gaussian mixture model-hidden Markov model, to obtain a corresponding acoustic feature intelligibility discrimination model, articulation motion feature intelligibility discrimination model and fusion feature intelligibility discrimination model.

Beneficial effects of the present invention are:

(1) According to the present invention, audio data and corresponding articulation motion data are acquired, acoustic features and corresponding articulation motion features are extracted respectively, feather fusion is performed on the acoustic features and the articulation motion features, and model training is performed through fusion feathers, so that a more accurate and reliable feather fusion evaluation result is obtained, which makes the articulation evaluation more objective and accurate.

(2) According to the present invention, training is further respectively performed according to the acoustic features and the articulation motion features to obtain an acoustic feature intelligibility discrimination model and an articulation motion feature intelligibility discrimination model. Policy fusion processing is performed on evaluation results of each model to obtain a fusion evaluation result, and the policy fusion evaluation result and the feature fusion evaluation result are mutually verified and cross-referenced, so that the articulation evaluation result is more objective and accurate.

(3) The present invention not only detects articulation motion data of the vocal organ, but also includes setting a space sensor at a head position to detect head motion data, and correcting the articulation motion data according to the head motion data, so that the data is more accurate and reliable.

BRIEF DESCRIPTION OF THE DRAWINGS

Accompanying drawings described herein are intended to provide a further understanding of the present invention, which constitutes a part of the present invention. Schematic embodiments of the present invention and the description thereof are intended to explain the present invention and do not constitute an undue limitation on the present invention.

In the accompanying drawings.

DESCRIPTION OF THE EMBODIMENTS

In order to make the technical problems to be solved, technical solutions and beneficial effects of the present invention clearer, the following will further describe the present invention in detail with reference to accompanying drawings and embodiments. It should be understood that the specific embodiments described herein are merely illustrative of the present application and are not intended to limit the present application.

Figure 1:
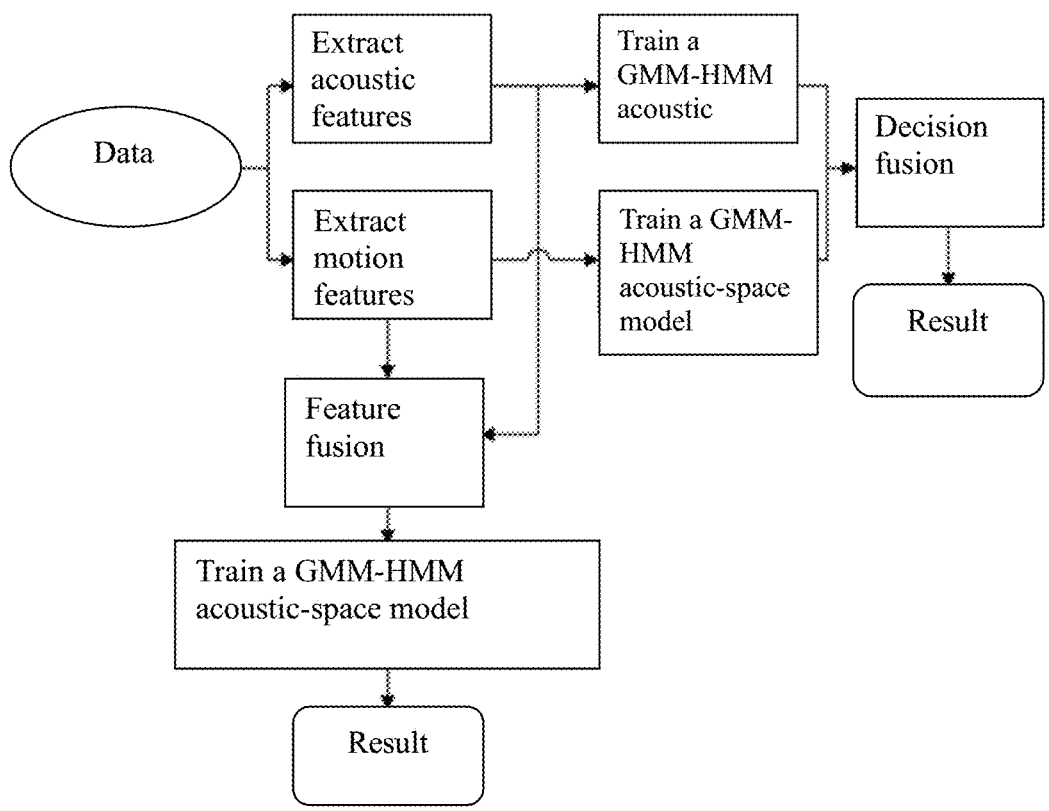
FIG. 1 is a simple flow diagram of an articulation evaluation method combining acoustic features and articulation motion features according to the present invention.

As shown in FIG. 1, an articulation evaluation method combining acoustic features and articulation motion features provided by the present invention includes the following steps:

Step (10): Acquire audio data and articulation motion data, extract acoustic features from the audio data, and extract articulation motion features from the articulation motion data, where the audio data and the articulation motion data correspond in time;

Step (20): Perform feature fusion processing on the acoustic features and the articulation motion features according to a time correspondence to obtain fusion features;

Step (30): Perform training according to the fusion features to obtain a fusion feature intelligibility discrimination model; and Step (40): Obtain a feature fusion evaluation result by using the fusion feature intelligibility discrimination model.

Step (50): Respectively perform training according to the acoustic features and the articulation motion features to obtain an acoustic feature intelligibility discrimination model and an articulation motion feature intelligibility discrimination model, and perform policy fusion processing on an evaluation result of the acoustic feature intelligibility discrimination model and an evaluation result of the articulation motion feature intelligibility discrimination model to obtain a policy fusion evaluation result.

The acquiring audio data and articulation motion data in step (10) is to acquire the audio data and the articulation motion data by using an electromagnetic articulation motion tracing system, which are, in this embodiment, articulation motion data and audio data acquired by using a 3DAG500 electromagnetic articulation motion tracing system (an EMA system); obtain the articulation motion data by placing space sensors at a vocal organ and calculating three-dimensional space coordinates and angles of the space sensors in a magnetic field, and acquire the audio data corresponding in time while acquiring the articulation motion data; where the vocal organ includes lips, and the articulation motion data includes lip motion data. Due to the abnormal movement of the tongue in patients with dysarthria, the sensor falls off in the movement process, which makes it difficult to obtain valid data of tongue motion data. Therefore, in this embodiment, lip motion data is selected as main articulation motion data.

The EMA system calculates three-dimensional space coordinates and angles of space sensors in the magnetic field by using the phenomenon that the space sensors generate an alternating current in an alternating magnetic field, and acquires motion data. Audio signals are acquired synchronously while position information of the space sensor is acquired. The space sensor is attached to a recording device by a thin and lightweight cable, so that the space sensor does not interfere with the free movement of a head inside an EMA cube.

The extracting acoustic features from the audio data in step (10) further includes:

Step (11): Perform pre-emphasis processing on the audio data s (n) through a high-pass filter to obtain weighted data; where a relationship of the high-pass filter can be expressed as $H(z)=1-az^{-1}([a \in [0.9,1])$; a pre-emphasized signal is expressed as $s'(n)=s(n)-as(n-1)$, and in this embodiment, the value of a is 0.95.

Step (12): Perform windowing processing on each frame of the weighted data to obtain windowed data; where in this embodiment, 20 ms is taken as one frame, and due to possible leakage of frequency spectrum energy at the position of the frame boundary, a Hanning window is selected to perform windowing processing on each frame.

Step (13): Perform fast Fourier transform (FFT) on each frame, convert time domain data to frequency domain data, and calculate spectral line energy.

Step (14): Make spectral line energy of each frame of the windowed data pass through a Mel filter, and calculate energy in the Mel filter.

Step (15): Calculate a discrete cosine transform (DCT) cepstrum after the logarithm of energy of the Mel filter is taken, to obtain a Mel frequency cepstral coefficient (MFCC).

Step (16): Obtain the acoustic features by using the Mel MFCC as a feature parameter.

The Mel MFCC is based on auditory frequency domain characteristics of the human ear to map a linear amplitude spectrum to a Mel nonlinear amplitude spectrum based on auditory perception and then perform conversion to the cepstrum. Change information between preceding and subsequent frames also helps to identify different speech characteristics, so the MFCC generally also adds a first-order difference and a second-order difference for each dimension of the cepstral coefficient. In this embodiment, a 13-dimensional MFCC and the first-order difference and second-order difference thereof are adopted as acoustic features.

The performing feature fusion processing in step (20) is to set a window length of the audio features and the articulation motion data according to a sampling rate of the audio data and the articulation motion data, set a window move according to the window length, and perform feature fusion on the acoustic features and the articulation motion features through the window move, so that modeling can be performed by effectively utilizing complementarity advantages of the two types of feature points. In this embodiment, the sampling rate of the audio data is 16000 Hz, and the sampling rate of the articulation motion data is 200 Hz. To synchronize the two types of features, the window length of the acoustic features is set to 20 ms, the window length of the motion features is 5 ms, and the window move during feature extraction is 5 ms. In this embodiment, the feature dimension of the obtained fusion features (Acoustic-Articulatory) is 51. A GMM-HMM model with four levels (normal, slight, medium, severe) of intelligibility discrimination is trained using the fusion features. The hidden Markov model has a state number of 3 and a mixed Gauss number of 24.

Preferably, in step (30), the model training is performed by respectively inputting the acoustic features, the articulation motion features or the fusion features into a Gaussian mixture model-hidden Markov model (GMM-HMM), to obtain a corresponding acoustic feature intelligibility discrimination model, articulation motion feature intelligibility discrimination model and fusion feature intelligibility discrimination model. By means of the GMM-HMM, training is performed by respectively utilizing the acoustic features and the articulation motion features to obtain an intelligibility discrimination model for discriminating different levels of intelligibility, and thus intelligibility evaluation is performed. Considering the timing characteristics of a speech signal, modeling is performed by using the HMM, and a state emission probability of each HMM is calculated using the GMM. This is the GMM-HMM. The degree of intelligibility is directly proportional to its severity. According to the diagnosis of a speech pathologist, the degree of intelligibility is divided into mild, medium, and severe, plus control of a normal human, a total of four groups. The GMM-HMM is trained for each group separately. In order to verify that the influence of different features on the intelligibility discrimination is different, the GMM-HMM is trained for acoustic features and articulation motion features respectively. The hidden Markov model is a left-to-right model without spanning. The hidden Markov model has a state number of 3 and a mixed Gauss number of 8, and an acoustic feature intelligibility discrimination model (labeled as Acoustic-GMM-HMM) and an articulation motion feature intelligibility discrimination model (labeled as Articulatory-GMM-HMM).

In step (40), the obtaining a feature fusion evaluation result by using the fusion feature intelligibility discrimination model is to determine different levels of intelligibility by using the fusion feature intelligibility discrimination model.

In step (50), the policy fusion processing is to set different weight ratios according to an evaluation result of the acoustic feature intelligibility discrimination model and an evaluation result of the articulation motion feature intelligibility discrimination model respectively, and calculate a policy fusion evaluation result according to the weight ratio; that is, decision fusion is performed on the acoustic feature intelligibility discrimination model (Acoustic-GMM-HMM) and an articulation motion feature intelligibility discrimination model (Articulatory-GMM-HMM) according to the following formula:

$$LL = \underset{k}{\operatorname{argmax}}\{w \times LL_{acoustic}^{k} + (1-w) \times LL_{articulatory}^{k}\};$$

where LL represents the policy fusion evaluation result (namely a maximum likelihood score after decision fusion), $LL_{acoustic}^{k}$ represents an evaluation result of the acoustic feature intelligibility discrimination model, $LL_{articulatory}^{k}$ represents an evaluation result of the articulation motion feature intelligibility discrimination model, k represents grade classification of the evaluation results, w represents a weight, and an argmax function represents looking for a parameter with a largest score; in this embodiment, k is 1, 2, 3 and 4, representing four levels of normal, slight, medium, and severe, respectively; w represents a weight of the acoustic feature intelligibility discrimination model, and the value is 0.5; and 1-w represents a weight of the articulation motion feature intelligibility discrimination model (Articulatory-GMM-HMM).

Figure 2:
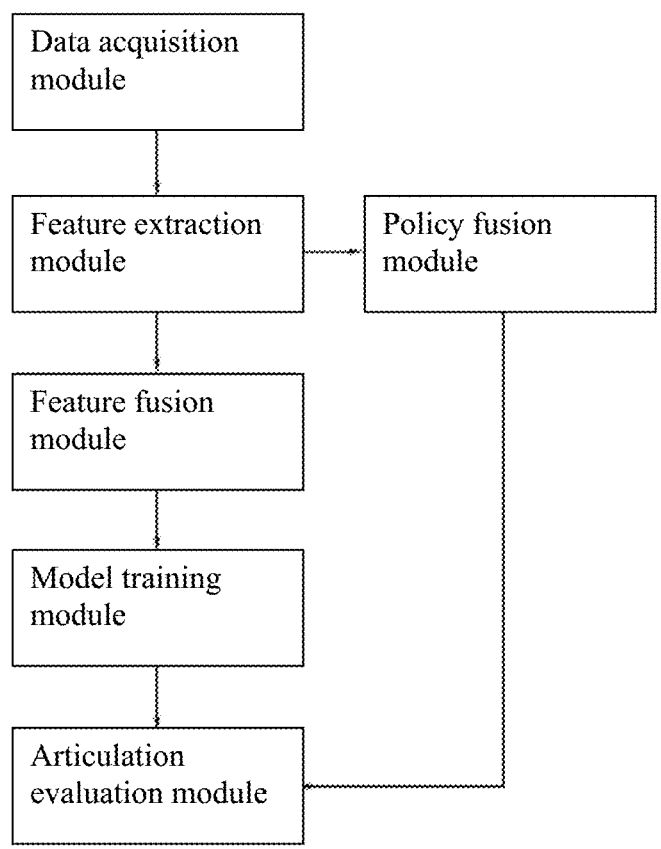
FIG. 2 is a schematic structural diagram of an articulation evaluation system combining acoustic features and articulation motion features according to the present invention.

As shown in FIG. 2, the present invention also provides an articulation evaluation system combining acoustic features and articulation motion features, including:

a data acquisition module, which acquires the audio data and the articulation motion data by using an electromagnetic articulation motion tracing system, obtains the articulation motion data by placing space sensors at a vocal organ and calculating three-dimensional space coordinates and angles of the space sensors in a magnetic field, and acquires the audio data corresponding in time while acquiring the articulation motion data;

a feature extraction module, configured to acquire audio data and articulation motion data, extract acoustic features from the audio data, and extract articulation motion features from the articulation motion data, where the audio data and the articulation motion data correspond in time;

a feature fusion module, configured to perform feature fusion processing on the acoustic features and the articulation motion features according to a time correspondence to obtain fusion features;

a model training module, configured to perform training according to the fusion features to obtain a fusion feature intelligibility discrimination model; and an articulation evaluation module, configured to obtain a feature fusion evaluation result by using the fusion feature intelligibility discrimination model;

a policy fusion module; where the model training module further respectively performs training according to the acoustic features and the articulation motion features to obtain an acoustic feature intelligibility discrimination model and an articulation motion feature intelligibility discrimination model, and the policy fusion module performs policy fusion processing on an evaluation result of the acoustic feature intelligibility discrimination model and an evaluation result of the articulation motion feature intelligibility discrimination model to obtain a policy fusion evaluation result.

Figure 3:
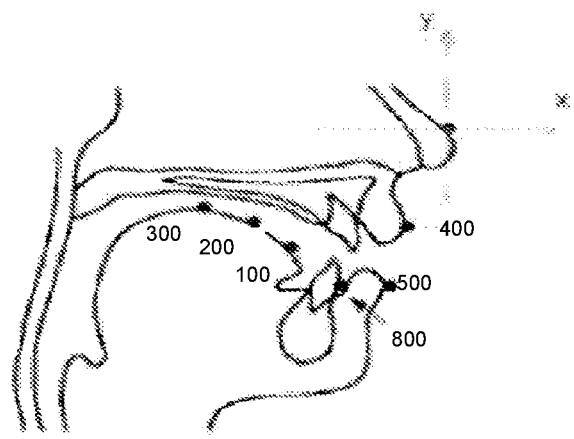
FIG. 3 is a first schematic distribution diagram of space sensors.
Figure 4:
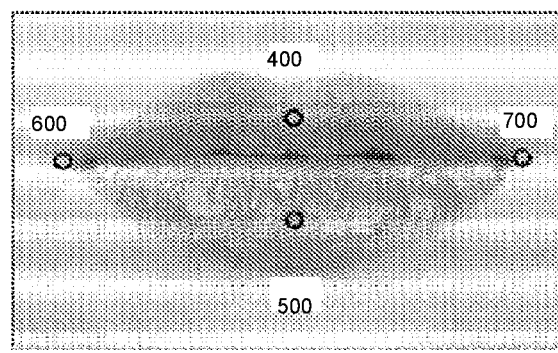
FIG. 4 is a second schematic distribution diagram of the space sensors.

As shown in FIGS. 3 and 4, in this embodiment, the vocal organ includes one or more of the following: a tongue, lips, mouth corners, and incisors; where space sensors of the tongue are disposed at the tip of the tongue (100) (1 cm behind the anatomical surface of the tongue), the center of the tongue (200) (3 cm behind the tongue tip sensor), and the back of the tongue (300) (2 cm behind the tongue center sensor); space sensors of the lips are disposed at the middle of the upper lip (400) and the middle of the lower lip (500); space sensors of the mouth corners are disposed at the left mouth corner (600) and the right mouth corner (700); and space sensors of the incisors are disposed on lower incisors (800) and used to track movements of a jaw. The vocal organ is mainly composed of the lips, teeth, the tongue, a palate, and the like. The tongue and lips work closely with other parts to block airflow and change the shape of an oral resonator, playing an important role in articulation. Therefore, data of the tongue vocal organ is first analyzed. However, due to the abnormal movement of the tongue in patients with dysarthria, the sensor falls off in the movement process, which makes it difficult to obtain valid data of tongue motion data. Therefore, in this embodiment, motion data of the lip vocal organ is selected as main articulation motion data.

Further, the articulation evaluation method also includes setting a space sensor at a head position to detect head motion data, and correcting the articulation motion data according to the head motion data; where the head position includes one or more of the following: a forehead, a nose bridge, and ear backs; where the space sensors of the ear backs are disposed on mastoid bones at the ear backs, playing a role in reference and recording of head movements.

In this embodiment, we make an analysis by using three-dimensional space coordinates collected by the space sensors. Further, a space sensor is placed on a nose bridge, and the extracting articulation motion features from the articulation motion features in step (10) is to use the space sensor on the nose bridge as a coordinate origin, and calculate relative distances between space sensors on lips and the coordinate origin; use three-dimensional coordinate distances x, y, z of four space sensors on the lips as motion features, use each sampling point as a frame, and extract articulation motion features from each frame of data according to the following formula:

$$\operatorname{lip}=[x_1 \ldots x_4, y_1 \ldots y_4, z_1 \ldots z_4]^T;$$

where subscripts of x, y, z represent upper lip motion data, lower lip motion data, left mouth corner motion data, and right mouth corner motion data, respectively. The articulation motion features have a total of 12 dimensions.

The model training module performs training by respectively inputting the acoustic features, the articulation motion features or the fusion features into a Gaussian mixture model-hidden Markov model, to obtain a corresponding acoustic feature intelligibility discrimination model, an articulation motion feature intelligibility discrimination model and a fusion feature intelligibility discrimination model.

In this embodiment, an algorithm flow of the system is simply described by taking a Torgo data set based on audio data and articulation motion data as an example. The specific steps are as follows:

1) Input of Torgo Data Sets

TABLE 1

Experimental data set information

| | Speech impediment | | | Normal person | |
|---|---|---|---|---|---|
| Label | Sample number | Intelligibility level | Sample number | Label | Sample number | Sample number |
| F01 | — | Severe | 567 | FC01 | 163 | 4289 |
| M01 | 100 | Severe | | FC02 | 999 | |
| M02 | 169 | Severe | | FC03 | 795 | |
| M04 | 298 | Severe | | MC01 | 614 | |
| M05 | 503 | Medium to severe | 876 | MC02 | 464 | |
| F03 | 373 | Medium | | MC03 | 600 | |
| F04 | 250 | Slight | 671 | MC04 | 654 | |
| M03 | 421 | Slight | | — | — | — |

As shown in Table 1, the input of the system includes four levels of intelligibility: severe, medium, slight, and normal. The level of intelligibility is determined according to a diagnosis of a speech pathologist. The numbers of subjects in the data sets were 3, 2, 2, and 7, respectively, and the numbers of articulation samples were 567, 876, 671, and 4289, respectively.

2) Extraction of Data Features

TABLE 2

Extracting feature conditions

| | Acoustic | Articulatory | A-A feature |
|---|---|---|---|
| Sampling frequency | 1.6 kHz | 0.2 kHz | — |
| Frame size | 20 ms | 5 ms | — |
| Frame shift | 5 ms | 5 ms | 5 ms |
| Dimension | 39 | 12 | 51 |

An EMA device acquires audio data and articulation motion data synchronously, and acoustic features, motion features and fusion A-A features of the two kinds of features are extracted respectively through settings of Table 2.

3): Training of an Intelligibility Discrimination Model

TABLE 3

Intelligibility discrimination evaluation result

| | Acoustic | Articulatory | Feature-fusion | Decision-fusion |
|---|---|---|---|---|
| Slight | 93.47% | 97.63% | 99.28% | 99.15% |
| Medium | 83.79% | 98.08% | 98.36% | 98.11% |
| Severe | 94.19% | 97.56% | 97.88% | 97.07% |
| Normal | 99.86% | 96.81% | 98.30% | 97.95% |
| Average | 96.50% | 97.06% | 98.21% | 98.00% |

After the audio features and the motion features of the data are acquired, the training of the intelligibility discrimination model is performed by using a GMM-HMM method.

As shown in the first two columns of Table 3, the discrimination accuracy of speech impediments is obviously improved through a GMM-HMM discrimination model using motion features, and but for normal persons, acoustic features using the MFCC have a higher accuracy. Overall, the GMM-HMM using motion features improved the accuracy by an average of 0.56% over the GMM-HMM using acoustic features. This indicates that the use of motion features is very effective in discriminating the intelligibility of speech impediments.

4) Model Training of Feature Fusion and Decision Fusion

TABLE 4

Intelligibility discrimination kappa coefficient index

| Acoustic | Articulatory | Feature-fusion | Decision-fusion |
|---|---|---|---|
| 0.930 | 0.944 | 0.968 | 0.962 |

Considering that the acoustic features have a good effect of discrimination of normal persons while the motion features have a good effect of discrimination of speech impediments, in order to better apply complementary functions of the two types of features, it is proposed to use feature fusion A-A features to train the GMM-HMM and use the acoustic feature GMM-HMM and the motion feature GMM-HMM for decision fusion. As shown in the last two columns of Table 3, feature fusion and decision fusion can combine the complementary advantages of the two types of features, further improving the discriminating effect.

The present invention not only utilizes audio data, but also uses articulation motion data of a speech impediment to determine the intelligibility level of the dysarthria from the aspect of articulation motion. The focus of articulation motion data is to extract features from feature data of a speech impediment. By data analysis, it is found that tongue motion data is unstable and difficult to obtain. Therefore, this embodiment mainly uses articulation motion data of lips as a main basis, and the degree of intelligibility of a speech impediment can be effectively distinguished.

At the same time, in the intelligibility evaluation of the speech impediment, a conventional method for utilizing acoustic features based on audio data is improved by extracting articulation motion features, and feasibility thereof is illustrated through Torgo data sets, accuracy and a kappa coefficient.

The present invention combines conventional speech acoustic features and articulation motion features through feature fusion and decision fusion, effectively utilizes the complementarity of the two types of features, and ensures the objectivity and comprehensiveness of the evaluation. By the fusion method, the results have a clear advantage in classifying the degree of intelligibility compared with results obtained by using acoustic features alone or using articulation motion features alone.

It should be noted that each embodiment in the specification is described in a progressive manner, and each embodiment focuses on differences from other embodiments, and the same or similar parts between the embodiments can be referred to each other. Since the system embodiment is basically similar to the method embodiment, the description is relatively simple, and the relevant parts can be referred to part of the description of the method embodiment. Moreover, herein, the term "comprise", "include", or any other variant thereof is intended to encompass a non-exclusive inclusion, such that a process, method, article, or device that includes a series of elements includes not only those elements, but also other elements not explicitly listed, or elements that are inherent to such a process, method, article, or device. Without more restrictions, an element defined by the phrase "including a . . . " does not exclude the presence of another same element in a process, method, article, or device that includes the element. In addition, those of ordinary skill in the art can understand that all or some of the steps of implementing the foregoing embodiments may be completed through hardware, or may be completed by instructing relevant hardware through a program. The program may be stored in a computer readable storage medium. The storage medium mentioned above may be a read-only memory, a magnetic disk or an optical disk or the like.

The foregoing description shows and describes the preferred embodiments of the present invention. It should be understood that the present invention is not limited to the forms disclosed herein, which should not be considered as an exclusion of other embodiments, but can be used for various other combinations, modifications and environments, and can be modified through the foregoing teachings or technology or knowledge in the related art within the scope of the inventive concept herein. The modifications and changes made by those skilled in the art do not depart from the spirit and scope of the present invention and should fall within the protection scope of the appended claims.

What is claimed is:

1. An articulation evaluation method combining acoustic features and articulation motion features to obtain an accurate and reliable fusion evaluation result for diagnosing dysarthria through speech intelligibility, comprising following steps:

Acquiring audio data and articulation motion data, extracting the acoustic features from the audio data, and extracting the articulation motion features from the articulation motion data, said audio data and said articulation motion data acquired by using a 3D AG500 electromagnetic articulation motion tracing system, and said articulation motion data also obtained by placing space sensors on a vocal organ to calculate three-dimensional space coordinates and angles of the space sensors in a magnetic field;

said extracting of the acoustic features and extracting of the articulation motion features performed by a feature extraction module configured to acquire the audio data and the articulation motion data, extract the acoustic features from the audio data, and extract the articulation motion features from the articulation motion data, wherein the audio data and the articulation motion data correspond in time;

Performing feature fusion processing on the acoustic features of the audio data and the articulation motion features of the articulation motion data according to the time to obtain fusion features utilizing a feature fusion module configured to perform functions;

Performing training according to the fusion features by inputting the acoustic features, the articulation motion features or the fusion features into a Gaussian mixture model-hidden Markov model (GMM-HMM) to obtain a fusion feature intelligibility discrimination model, said performing the training according to the fusion features by utilizing a model training module configured to perform said functions; and Obtaining a feature fusion evaluation result using an articulation evaluation module configured to obtain said feature fusion evaluation result by using the fusion feature intelligibility discrimination model, wherein where the vocal organ is a tongue, the space sensors are disposed at a tip of the tongue, a center of the tongue, and a back of the tongue;

wherein where the vocal organ is lips, the space sensors are disposed at a middle of an upper lip and a middle of a lower lip; and wherein where the vocal organ is a mouth, the space sensors are disposed at a left mouth corner and a right mouth corner; and wherein where the vocal organ is incisors, the space sensors are disposed on lower incisors of a jaw.

2. The articulation evaluation method of claim 1, wherein the training is further respectively performed according to the acoustic features of the audio data and the articulation motion features of the articulation motion data to obtain an evaluation result of an acoustic feature intelligibility discrimination model and an evaluation result of an articulation motion feature intelligibility discrimination model, and policy fusion processing is performed on the evaluation result of the acoustic feature intelligibility discrimination model and the evaluation result of the articulation motion feature intelligibility discrimination model to obtain a policy fusion evaluation result.

3. The articulation evaluation method of claim 1, wherein said extracting the articulation motion features from the articulation motion data further requires that a space sensor of the space sensors is also placed on a nose bridge, as a coordinate origin in order to calculate relative distances between the space sensors on the lips and the coordinate origin; said calculation the relative distances requires three-dimensional coordinate distances x, y, and z of four space sensors on the lips as the articulation motion features, using each sampling point of sampling points as a frame, and extracting the articulation motion features from each frame of frames of the articulation motion data according to following formula:

lip=[x1 . . . x4, y1 . . . y4, z1 . . . z4]T; wherein subscripts of x, y, and z represent upper lip motion data, lower lip motion data, left mouth corner motion data, and right mouth corner motion data, respectively.

4. The articulation evaluation method of claim 1, wherein the performing of the feature fusion processing on the acoustic features of the audio data and the articulation motion features of the articulation motion data requires setting a window length of the acoustic features of the audio data and the articulation motion features of the articulation motion data according to a sampling rate of the audio data and the articulation motion data, setting a window move according to the window length, and performing the fusion features on the acoustic features and the articulation motion features through the window move.

5. An articulation evaluation method combining acoustic features and articulation motion features to obtain an accurate and reliable fusion evaluation result for diagnosing dysarthria through speech intelligibility, comprising following steps:

Acquiring audio data and articulation motion data, extracting the acoustic features from the audio data, and extracting the articulation motion features from the articulation motion data, wherein the audio data and the articulation motion data correspond in time;

Performing feature fusion processing on the acoustic features of the audio data and the articulation motion features of the articulation motion data according to the time to obtain fusion features utilizing a feature fusion module configured to perform functions;

Performing training according to the fusion features by inputting the acoustic features, the articulation motion features or the fusion features into a Gaussian mixture model-hidden Markov model (GMM-HMM) to obtain a fusion feature intelligibility discrimination model, said performing the training according to the fusion features by utilizing a model training module configured to perform said functions; and Obtaining a feature fusion evaluation result using an articulation evaluation module configured to obtain said feature fusion evaluation result by using the fusion feature intelligibility discrimination model, wherein the training is further respectively performed according to the acoustic features of the audio data and the articulation motion features of the articulation motion data to obtain an evaluation result of an acoustic feature intelligibility discrimination model and an evaluation result of an articulation motion feature intelligibility discrimination model, and policy fusion processing is performed on the evaluation result of the acoustic feature intelligibility discrimination model and the evaluation result of the articulation motion feature intelligibility discrimination model to obtain a policy fusion evaluation result; and wherein the policy fusion processing requires setting different weight ratios according to the evaluation result of the acoustic feature intelligibility discrimination model and the evaluation result of the articulation motion feature intelligibility discrimination model respectively, and calculating the policy fusion evaluation result according to said weight ratios using following calculation formula:

$$LL = \mathrm{argmax}\ 'k'\{w*LL'k'\mathrm{acoustic} + (1-w)*LL'k'\mathrm{articulatory}\};$$

Wherein LL represents the policy fusion evaluation result; LL'k'acoustic; represents the evaluation result of the acoustic feature intelligibility discrimination model, LL'k'articulatory represents the evaluation result of the articulation motion feature intelligibility discrimination model, k represents grade classification of the evaluation result of the acoustic feature intelligibility discrimination model and the evaluation result of the articulation motion feature intelligibility discrimination model, w represents a weight, and an argmax function represents looking for a parameter with a largest score.

6. An articulation evaluation system combining acoustic features and articulation motion features to obtain an accurate and reliable fusion evaluation result for diagnosing dysarthria through speech intelligibility, comprising:

a feature extraction module, configured to acquire audio data and articulation motion data, extract the acoustic features from the audio data, and extract the articulation motion features from the articulation motion data, wherein the audio data and the articulation motion data correspond in time;

a feature fusion module, configured to perform feature fusion processing on the acoustic features from the audio data and the articulation motion features from the articulation motion data according to the time to obtain fusion features;

a model training module, configured to perform training according to the fusion features to obtain a fusion feature intelligibility discrimination model; and an articulation evaluation module, configured to obtain a feature fusion evaluation result by using the fusion feature intelligibility discrimination model, and a 3D AG500 electromagnetic articulation motion tracing system, wherein the audio data and the articulation motion data acquired by using the 3D AG500 electromagnetic articulation motion tracing system, and the articulation motion data obtained by placing a plurality of spacing sensors adapted and assigned for placement on a vocal organ, wherein where the vocal organ is a tongue, the spacing sensors are disposed at a tip of the tongue, a center of the tongue, and a back of the tongue;

wherein where the vocal organ is lips, the spacing sensors are disposed at a middle of an upper lip and a middle of a lower lip; and wherein where the vocal organ is a mouth, the spacing sensors are disposed at a left mouth corner and a right mouth corner; and wherein where the vocal organ is incisors, the spacing sensors are disposed on lower incisors of a jaw.

7. The articulation evaluation system of claim 6, further comprising a policy fusion module;

wherein the model training module further performs the training according to the acoustic features of the audio data and the articulation motion features of the articulation motion data to obtain an acoustic feature intelligibility discrimination model and an articulation motion feature intelligibility discrimination model; and the policy fusion module performs policy fusion processing on an evaluation result of the acoustic feature intelligibility discrimination model and an evaluation result of the articulation motion feature intelligibility discrimination model to obtain a policy fusion evaluation result, and wherein the policy fusion module sets different weight ratios according to the evaluation result of the acoustic feature intelligibility discrimination model and the evaluation result of the articulation motion feature intelligibility discrimination model respectively, and calculates the policy fusion evaluation result according to said weight ratios using following calculation formula:

$$LL = \mathrm{argmax}\ 'k'\{w*LL'k'\mathrm{acoustic} + (1-w)*LL'k'\mathrm{articulatory}\};$$

Wherein LL: represents the policy fusion evaluation result; LL'k'acoustic: represents the evaluation result of the acoustic feature intelligibility discrimination model, LL'k'articulatory represents the evaluation result of the articulation motion feature intelligibility discrimination model, k represents grade classification of the evaluation result of the acoustic feature intelligibility discrimination model and the evaluation result of the articulation motion feature intelligibility discrimination model, w represents a weight, and an argmax function represents looking for a parameter with a largest score.

8. The articulation evaluation system of claim 7, further comprising a data acquisition module, wherein the data acquisition module acquires the audio data and the articulation motion data by using an electromagnetic articulation motion tracing system, obtains the articulation motion data by placing the spacing sensors at the vocal organ and calculating three-dimensional space coordinates and angles of the spacing sensors in a magnetic field, and acquires the audio data to the time while acquiring the articulation motion data.

9. The articulation evaluation system of claim 8, further comprising at least one spacing sensor set at a head position to detect head motion data and to correct the articulation motion data according to the head motion data;

wherein the head position comprises one or more of following: a forehead, a nose bridge, and backs of ears; and wherein when the at least one spacing sensor is disposed on the backs of the ears said at least one spacing sensor is placed on mastoid bones.

10. The articulation evaluation system of claim 6, wherein the model training module performs the training by respectively inputting the acoustic features of the audio data, the articulation motion features of the articulation motion data or the fusion features into a Gaussian mixture model-hidden Markov model, to obtain a corresponding acoustic feature intelligibility discrimination model, articulation motion feature intelligibility discrimination model and fusion feature intelligibility discrimination model.

* * * * *